United States Patent [19]

Durham

[11] 4,200,320
[45] Apr. 29, 1980

[54] CONTACT LENS APPLICATOR

[76] Inventor: Henry B. Durham, 405 Chestnut St., Birmingham, Ala. 35206

[21] Appl. No.: 914,591

[22] Filed: Jun. 12, 1978

[51] Int. Cl.² ............................................... A61F 9/00
[52] U.S. Cl. .................................... 294/1 CA; 294/25
[58] Field of Search .............. 294/1 CA, 25, 33, 64 R; 128/303 R; 206/5.1; 351/160

[56] References Cited
U.S. PATENT DOCUMENTS

| 1,316,436 | 9/1919 | Feeney ................................... 294/25 |
| 3,132,887 | 5/1964 | Martinez ...................... 294/1 CA X |
| 3,177,874 | 4/1965 | Spriggs ............................... 294/25 X |
| 3,490,806 | 1/1970 | Lopez-Calleja et al. ......... 294/1 CA |
| 3,583,010 | 6/1971 | Woodrum ..................... 294/1 CA X |
| 3,645,576 | 2/1972 | Horres .............................. 294/1 CA |

*Primary Examiner*—Johnny D. Cherry
*Attorney, Agent, or Firm*—C. A. Phillips

[57] ABSTRACT

A contact lens applicator in which a lens holding ring is supported by two parallel and extremely flexible members which extend from opposite sides of the ring and attach to a handle.

5 Claims, 4 Drawing Figures

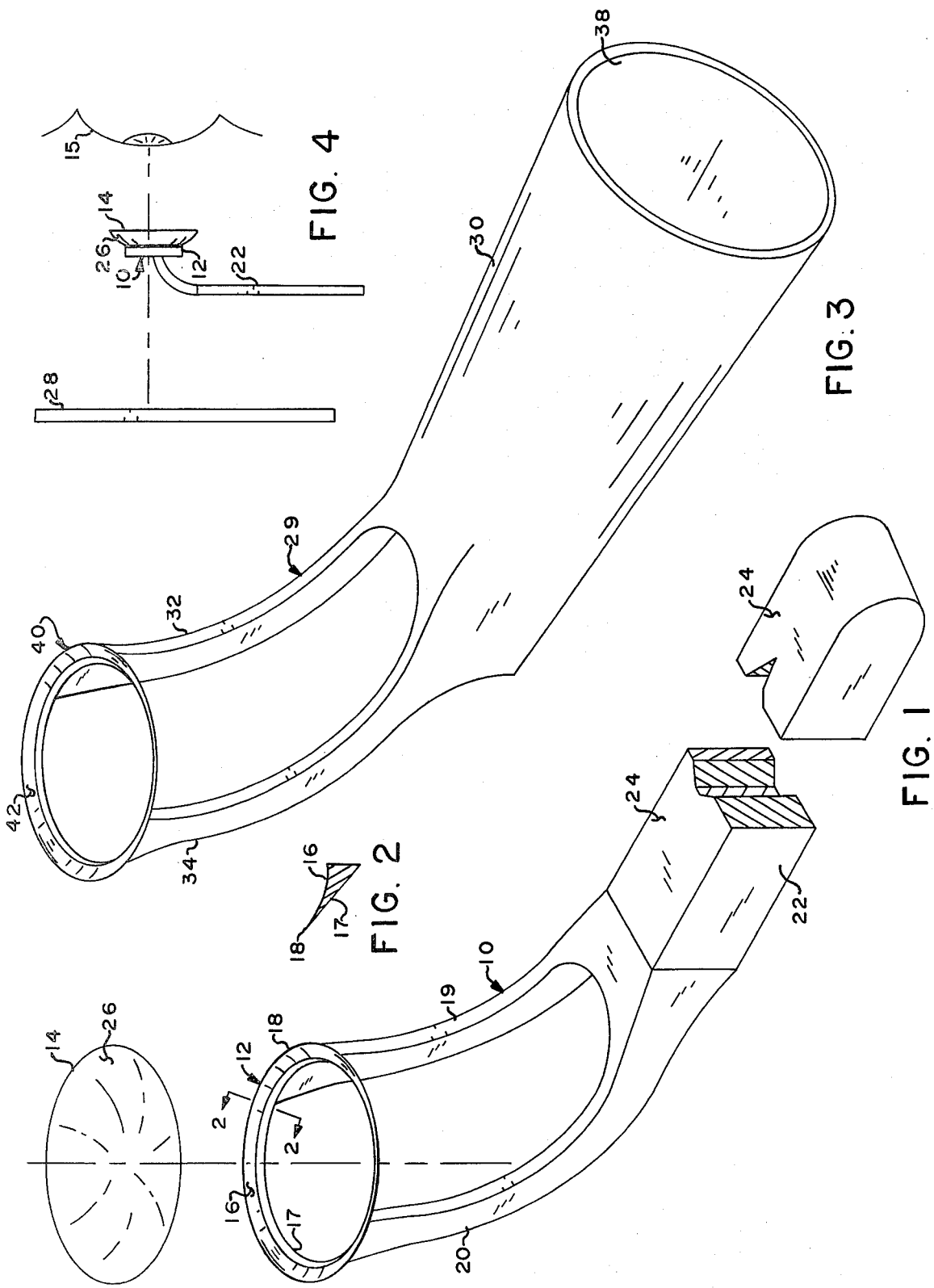

CONTACT LENS APPLICATOR

BACKGROUND OF THE INVENTION

1. Field of the Invention

This invention relates to contact lens applicators, and more particularly to an improved applicator by which a lens can be readily placed in contact with the eye accurately and without discomfort.

2. General Description of the Prior Art

The most frequently used procedure for placing a contact lens in the eye is to place a moistened contact lens on the tip of an index finger and then to move the finger toward the eye, endeavoring to effect a correct positioning of the finger. Usually the progress of the finger and lens toward the eye is followed in a mirror.

One of the difficulties encountered has been that the moistened lens tends to shift its position on the moistened fingertip and thus prevent accurate positioning of the lens.

Another difficulty is that the broadness of the fingertip holding the lens may completely block the mirror-viewed image. This occurs by first blocking the vision of the eye receiving the lens and finally blocking the vision of the opposite eye which would be helping in the application of the lens.

The problems noted above are compounded in instances where vision is substantially impaired as in cases where cataracts have been formed or are forming, or where cataracts have been removed by surgery, leaving drastically reduced vision.

Further, there is the problem of comfortably engaging one's eye with one's finger. It is a procedure which one is most reluctant to follow in view of normal discomfort which occurs when there is relatively firm contact between anything and the eye. It is simply not easy to move the finger with a sufficiently light touch to avoid this from occurring.

In an apparent recognition of at least a part of the problem, there has recently appeared a contact lens applicator consisting of a tubular lens holder adapted to fit on the end of a penlight type flashlight. This device is thus intended to overcome one of the problems, that of positioning, it being assumed that by virtue of light passing through the holder and contact lens of the holder that one can center the lens in the eye. Actually, however, the lens holder may be moved about considerably without one detecting that it has been moved off center significantly with respect to the eye.

In addition to the penlight attachment type applicator described above, there has recently appeared on the market a finger-held applicator employing a solid cup on which the lens is placed. It is particularly intended as a device for the insertion of "soft" contact lenses which are flexible, unlike the rigid or "hard" contact lenses. This device is sold under the trademark "Soft-Sert". While it apparently offers the advantage of preventing a lens from falling or inverting while inserted, it still does not provide alignment assistance, nor does it significantly reduce the problem of positive contact transmitted between a finger and the eye.

Accordingly, it is an object of this invention to overcome the aforesaid and other difficulties with existing devices and to provide an improved contact lens applicator.

SUMMARY OF THE INVENTION

In accordance with this invention, a contact lens applicator is constructed in which a lens holding ring is supported on a handle by a flexible coupling, the flexible coupling being configured to separate the ring and handle in two dimensions, one being a dimension generally parallel to the plane of the ring, and the other dimension being generally perpendicular to the plane of the ring.

BRIEF DESCRIPTION OF THE DRAWINGS

FIG. 1 is a broken, exploded pictorial view of the embodiment of the invention and a contact lens.

FIG. 2 is a sectional view along lines 2—2 of FIG. 1.

FIG. 3 is a pictorial view of an alternate version of the embodiment.

FIG. 4 is a partially schematic, partially diagrammatic view of the embodiment as used.

DETAILED DESCRIPTION OF THE DRAWINGS

Referring to FIG. 1, lens applicator 10 employs a circular ring 12, which is sufficiently rigid to maintain its form with a contact lens 14 in place, and slightly smaller than a contact lens. As shown, upper surface 16 of ring 12 is bevelled to match a convex contour of lens 14, and the lower side 17 is tapered as shown in FIG. 2 so that the outer edge 18 terminates in a feathered edge. When moistened, lens 14 will adhere to ring 12 due to the cohesive force or capillary action present and the complementary shaped surfaces of the ring and lens.

Ring 12 is supported by two bendable and extremely flexible rubber-like support or coupling members 19 and 20. Support members 19 and 20 are attached to ring 12 180° apart and extend in a spaced fashion generally normal to the plane of ring 12 and then curve approximately 80° to terminate in integral, elongated handle 22. Sufficient distance is maintained between support members 19 and 20, and handle 22 is sufficiently distant from the axis of ring 12, to provide a clear view along this axis and through the center of ring 12.

Handle 12 is of a convenient length (e.g., 3½ to 4 inches) for holding and is positioned via the curved portions of support members 19 and 20, with its longitudinal axis forming an angle of approximately 10° (approximately parallel) with respect to a plane parallel to the plane of ring 12; and the plane of top surface 24 of handle 22 is spaced ¾ to 1¼ inches from the plane of ring 12. By this configuration, the eyelid of the left eye may be held open by fingers on the left hand, and then by the right hand (generally positioned in front of the right eye), applicator 10 may be moved with ring 12 in front of the left eye and between the fingers holding the eyelid open, whereby the ring, and thus a contact lens, may be moved up to that eye. Thus, the nose and the fingers holding the eyelid are avoided as obstacles by the configuration of the applicator. This procedure is equally applicable to the right eye by simply exchanging the terms left and right in the above.

In use, and referring additionally to FIG. 4, lens 14 is moistened and placed with the convex side up on a clean horizontal surface (not shown). Applicator 10 is then held by handle 22, and ring 12 is pressed down upon lens 14, allowing bevelled portion 26 to seat upon and adhere to ring 12 by capillary action. The user can now lift lens 14 with applicator 10 and use the fingers on his other hand to hold the eyelids of one eye open. The user, by peering through lens 14 and circular ring 12, can see a reflection in mirror 28, and thus align the applicator and lens with his eye. In accordance with this procedure, and wherein the contact lens used provides significant magnification, this magnification may be utilized in positioning ring 12 and the lens held thereby. This would be a typical case where a person has had a cataract or cataracts removed, and thereafter, for a period, used thick tempering glasses.

As a lens 14 is brought to and into contact with the eye 15, support members 19 and 20 will flex, allowing the lens to seat itself evenly and with gentle pressure on the eye. Because the eye offers a larger area for adhesion than does ring 12, lens 14 will adhere to the eye, and as the applicator is moved away from the eye, it disengages from the lens.

FIG. 3 illustrates an alternate form of the invention in applicator 29 wherein the handle, handle 30, is formed of a longitudinal tube which may be formed of the same flexible material as curved support members 32 and 34. Handle 30 tapers slightly from members 32 and 34 to have a larger open end 38 which, due to the tube's taper and flexible nature, is readily adaptable to fit over different sized fingers. Aside from the different handle configuration, this embodiment is generally identical with that shown in FIG. 1. Thus, ring 40 has a bevelled surface 42, and curved support members 32 and 34 which attach ring 40 to tubular handle 30.

Applicator 29 is used in the same manner as applicator 10 except that instead of grasping a handle, the user inserts his index finger in opening 38 with his fingernail facing downward with the applicator in the position shown. This allows the user to operate the applicator as an extension of his index finger. This offers the advantage that users who have formerly simply used their index finger to directly position a contact lens on an eye, for lack of a better method, find this applicator quite natural to use.

Having thus described my invention, what is claimed is:

1. A contact lens applicator comprising:
    a circular ring having a region on one side which is bevelled to generally conform to a convex surface of a contact lens;
    an elongated handle; and
    support means comprising a pair of spaced flexible and bendable coupling members, said coupling members extending from diametrically opposed regions of said ring to said handle, first in a direction generally normal to the plane of said ring leaving an open region of view through, and normal to, said ring and unobstructed by said coupling members, and then said coupling members extending in a direction having a directional component along a line parallel with the plane of said ring;
    whereby, when used, one may sight through a lens supported by said ring into a mirror, enabling an accurate and close positioning of the lens in front of the eye, and upon contact with the eye, said coupling is readily bendable, and thus there is no positive force applied to the eye.

2. A contact lens applicator as set forth in claim 1 wherein said handle comprises a stretchable tube, the end region of which is open and adapted to be worn over a finger.

3. A contact lens applicator as set forth in claim 1 wherein said handle is a generally rigid member.

4. A contact lens applicator as set forth in claim 3 wherein the distance between a first plane, a plane generally coincident with said ring, and a second plane, a plane lying along the closest elongated surface of said handle to said first plane, is ¾ to 1¼ inches.

5. A contact lens applicator as set forth in claim 1 wherein the opposite side of said ring is tapered, terminating in an outer peripheral edge which is a feathered edge.

* * * * *